United States Patent [19]

Holick

[11] Patent Number: 5,744,128
[45] Date of Patent: Apr. 28, 1998

[54] USE OF EMU OIL FOR STIMULATING SKIN AND HAIR GROWTH

[76] Inventor: Michael F. Holick, 31 Bishop La., Sudbury, Mass. 01776

[21] Appl. No.: 433,789

[22] Filed: May 3, 1995

[51] Int. Cl.$^6$ .............................. A61K 7/44; A61K 35/12
[52] U.S. Cl. ................................. 424/60; 424/522
[58] Field of Search ............................ 424/60, 522

[56] References Cited

U.S. PATENT DOCUMENTS

| | | | |
|---|---|---|---|
| 4,717,721 | 1/1988 | DeLuca et al. | 514/167 |
| 4,847,012 | 7/1989 | DeLuca et al. | 260/397.2 |
| 4,851,401 | 7/1989 | DeLuca et al. | 514/167 |
| 4,927,815 | 5/1990 | DeLuca et al. | 514/167 |
| 5,037,816 | 8/1991 | Holick et al. | 514/167 |
| 5,276,061 | 1/1994 | DeLuca et al. | 514/844 |
| 5,431,924 | 7/1995 | Ghosh et al. | 424/522 |
| 5,472,713 | 12/1995 | Fein et al. | 424/522 |

FOREIGN PATENT DOCUMENTS

| | | |
|---|---|---|
| WO 92/04039 | 3/1992 | WIPO . |
| WO 92/08470 | 5/1992 | WIPO . |

OTHER PUBLICATIONS

A portion of a column entitled "Industry Happenings," *Drug & Cosmetic Industry (DCI)* 154(5):97–98 (complete column, pp. 88–104) (May 1994).

Article entitled "Skincare Company Formed," *Soap/Cosmetics/Chemical Specialties*, issue of Jun. 1994, pp. 147–148.

Holick, M.F., et al., "A Parathyroid Hormone Antagonist Stimulates Epidermal Proliferation and Hair Growth in Mice," *Proc. Natl. Acad. Sci. USA* 91:8014–8016 (Aug. 1994).

Kutner, A., et al., "Novel Convergent Synthesis of Side–Chain–Modified Analogues of 1α, 25–Dihydroxycholecalciferol and 1α, 25–Dihydroxyergocalciferol," *J. Org. Chem.* 53:3450–3457 (1988).

Column entitled "The Compounder. Compounding Materials," *Drug & Cosmetic Industry (DCI)* 153(6):52 (Dec. 1993).

*Primary Examiner*—Nathan M. Nutter
*Attorney, Agent, or Firm*—Sterne, Kessler, Goldstein & Fox, P.L.L.C.

[57] ABSTRACT

The present invention is directed to the discovery that topical or parenteral administration of emu oil to a mammal stimulates the proliferation of skin. Emu oil can be used to treat skin wrinkles and rejuvenate aged and photo-damaged skin. It has also been discovered that emu oil can be topically applied to stimulate melanogenesis in the skin and to stimulate hair growth. Thus, emu oil is useful to treat pigmentation disorders such as hypopigmentation, stimulating melanogenesis to enhance skin tanning, and treating disorders relating to disturbances in hair cycling such as alopecia, male pattern baldness, female baldness, and chemotherapy-induced alopecia.

10 Claims, 2 Drawing Sheets

USE OF EMU OIL FOR STIMULATING SKIN AND HAIR GROWTH

BACKGROUND OF THE INVENTION

1. Field of the Invention

The invention relates to methods of topically, orally or parenterally applying emu oil or a fraction thereof to mammalian skin or hair for the purposes of stimulating skin and hair growth, or to enhance pigmentation of the skin. The invention further relates to compositions for topical, oral or parenteral application that are useful for treating skin disorders, said compositions comprising emu oil in combination with other substances known to have therapeutic effects on mammalian skin.

For the purposes of this specification, the term "emu oil" refers to oils and preparations of oils derived from the emu (*Dromais Novae—Hollandiae*).

2. Related Art

International application WO92/08470, published May 29, 1992, discloses pharmaceutical compositions including emu oil and dermal transport enhancing compounds that are useful as topical anti-inflammatory treatments. The published application also discloses the isolation of a biologically active fraction of emu oil that displays topical anti-inflammatory activity. The inventors surmise that the potent anti-elastase activity demonstrated to be present in the emu oil could provide a local anti-inflammatory, as well as an anti-degenerative effect, to dermal tissues that could be particularly relevant during dermal inflammation where cell and tissue damage produced by exposure to strong UV radiation, as in sunburn, occurs.

Oils extracted or rendered from emu body fats are known to contain triglyceride esters of long chain fatty acids including oleic acid and linoleic acid as well as the saturated fatty acids, palmitic acid and stearic acid. See Hilditch, T. P. and Williams, P. N., *The Chemical Constitution of Natural Fats*, 4th Edition, Chapman and Hall, London (1964). Emu oil is predominantly composed of triglyceride esters of saturated and unsaturated fatty acids. The overall fatty acid composition of emu oil preparations is not too dissimilar to that of chicken. However, while chicken oils are colorless, emu oils are invariably yellow colored. Mammalian fats are known to provide a depot for other naturally occurring lipophilic compounds. These compounds would include the fat soluble vitamins such as vitamin A, D and E as well as their precursors and metabolites. The natural diet of the emu consists of seeds, berries, grasses, leaves and plants present within the Australian bush which would be expected to contain a large variety of carotenoids, vitamins, terpenes, saponagens, flavones and other naturally occurring bioactive occurring compounds.

SUMMARY OF THE INVENTION

It has now been found that effective treatment of various skin and hair loss conditions can be achieved with compositions that include an effective amount of emu oil or a biologically active fraction thereof. It has been discovered that application of emu oil can: stimulate the proliferation of cells in mammalian skin tissue, stimulate melanogenesis in mammalian skin tissue, and stimulate hair follicle development and growth in mammalian skin tissue.

In one embodiment, the present invention relates to a method for treating skin conditions of skin slackness, wrinkles, dry skin, and insufficient sebum secretion comprising topically or parenterally applying to the skin of a mammal a composition comprising emu oil or a biologically active fraction thereof.

In a second embodiment, the present invention relates to a cosmetic preparation for skin rejuvenation and hydration comprising emu oil, or a biologically active fraction thereof, and one or more active vitamin D compounds.

In a third embodiment, the present invention relates to a method for treating hypopigmentation disorders by topically or parenterally administering to the skin of a mammal a composition comprising a pigmentation-increasing amount of emu oil, or a biologically active fraction thereof.

In a fourth embodiment, the present invention relates to a method for enhancing skin tanning of mammalian skin by applying a composition comprising emu oil, or a biologically active fraction thereof, to mammalian skin and/or hair in an amount effective to enhance skin tanning.

In a fifth embodiment, the present invention relates to a method for stimulating growth of mammalian hair comprising applying a composition comprising emu oil, or a biologically active fraction thereof, to the skin and/or hair of a mammal in an amount effective to stimulate hair growth.

In a sixth embodiment, the present invention relates to a method of accelerating the healing of topical wounds by topically or parenterally applying a composition comprising emu oil, or biologically active fraction thereof, and one or more parathyroid hormone peptides to a wound.

In a seventh embodiment, the present invention relates to a method of treating burns by topically applying a composition comprising emu oil, or a biologically active fraction thereof, and one or more parathyroid hormone peptides to a burn.

In an eighth embodiment, the present invention relates to a method for inhibiting cell proliferation and inducing cell differentiation in a mammal suffering from psoriasis, or cancer or precancer of the skin by topically or parenterally applying emu oil, or a biologically active fraction thereof, in admixture with a PTH/PTHrP peptide selected from the group consisting of PTH (1–34), PTH (3–34) and PTHrP (1–34).

Other features and advantages of the invention will be apparent from the following description of the preferred embodiments thereof, and from the claims.

DETAILED DESCRIPTION OF THE PREFERRED EMBODIMENTS

Figure 1:
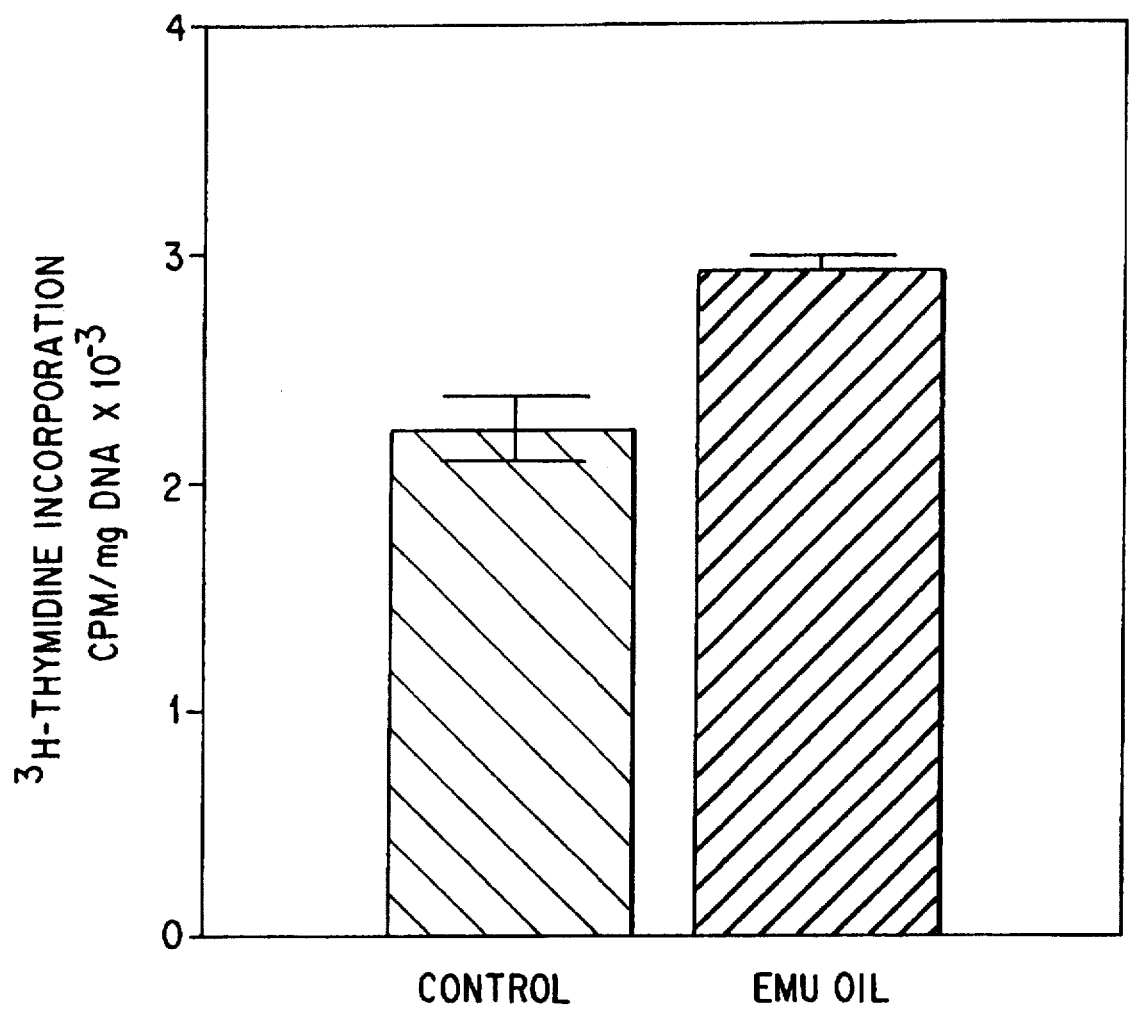
FIG. 1 is a bar graph that shows the effect of topical administration of emu oil on tritiated thymidine ($^3$H-thymidine) incorporation into the skin of C57 BL/6 mice, versus topical administration of corn oil.

One aspect of the present invention generally involves enhancing proliferation of a mammalian cell by contacting the cell with emu oil or biologically active fraction thereof. This aspect of the present invention has particular application in the promotion of skin growth in patients with skin ulcerations, as well as in the stimulation of epidermal regrowth in people who have decreased epidermal cell proliferation due to aging. Additionally, this aspect of the invention has cosmetic applications in rejuvenating aged and photodamaged skin.

A second aspect of the present invention generally involves enhancing melanogenesis in mammalian skin tissue by contacting the skin tissue with emu oil or a biologically active fraction thereof. This aspect of the invention has particular utility in treating pigmentation disorders such as hypopigmentation disorders, and for enhancing skin tanning.

A third aspect of the present invention generally involves enhancing hair follicle development and growth in mammalian skin tissue by contacting the skin tissue with emu oil or a biologically active fraction thereof. Alopecia, the disease of hair loss, may arise from various causes. In each instance, individual hairs cannot complete their normal hair cycle to reach the telogen state. In order to decrease baldness and accelerate hair generation, it is necessary to bring the hair follicles from the telogen state into the normal anagen state. It has now been found that hair growth is stimulated by administering to a mammal emu oil or a biologically active fraction thereof. This aspect of the present invention has particular utility in the promotion of new hair growth or stimulation of the rate of hair growth, e.g., following chemotherapeutic treatment or for treating a form of alopecia, e.g., male pattern baldness and female hair loss.

For the purposes of this specification, the term "emu oil" refers to oils and preparations of oils derived from the emu (*Dromais Novae—Hollandiae*). The emu oil, its partially purified active fractions or the active components themselves may be administered to mammals and man topically or parenterally.

The term "biologically active fraction" of emu oil includes those fractions or active components of emu oil that are useful as therapeutic agents in treating disorders such as aging, photodamaged skin and skin ulcerations, where a maintenance or stimulation of cell proliferation is desired. The ability of a particular fraction or component to maintain or stimulate cell proliferation can be determined by measuring the effect of a particular function or component on $^3$H-thymidine incorporation into the skin of mice. See, Holick et al., *Proc. Natl. Acad. Sci. USA* 91:8014–8016 (1994). The term "biologically active fraction" also includes fractions or active components that cause an increase in skin pigmentation and/or hair growth as determined by the method described in the Example herein.

Emu oil is commercially available from Emu Products, Western Australia Pty. Ltd., Perth, Australia, or from New World Technology, Inc., Greenwich, Conn., under the name "Kalaya oil." Active emu oil fraction can be isolated according to the following procedure disclosed in PCT published application WO92/08470. Emu oil is diluted 1:1 with hexane and fractionated on an activated florisil column (1 g of oil per 12 g of florisil). Additional hexane (100 ml per g of oil) is passed through the column followed by dichloromethane (100 ml per g of oil) and 10% methanol in dichloromethane (100 ml per g of oil). The material eluting in the hexane and the dicholoromethane fraction (0.89 g) is colorless and the material eluting in the 10% methanol in dichloromethane fraction (0.11 g) was a yellow color.

The material eluting in the 10% methanol in dichloromethane fraction is diluted 1:1 with hexane and applied to a silica column (1 g of yellow material per 12 g of silica). Additional hexane (100 ml per g of oil) is passed through the column followed by dichloromethane (100 ml per g of oil) and 10% methanol in dichloromethane (100 ml per g of oil).

The material eluting in the hexane and the dichloromethane fraction is colorless (0.64 g) and the material eluting in the 10% methanol in dichloromethane fraction (0.36 g) is a yellow color. Pure yellow component is separated from the methanol/dichloromethane by evaporation.

If the 10% methanol in dichloromethane fraction from the silica column is analyzed by gas chromatography using an on-column injection technique, the material is shown to be free of triglycerides, consisting principally of two closely eluting peaks. These two peaks correspond to two peaks observed when the unpurified oil is analyzed using the same technique.

Hydrolysis with sodium methoxide of the 10% methanol in dichloromethane fraction from the silica column shows that this fraction is composed of saturated and unsaturated fatty acids esterified with a series of unidentified compounds. Indications are that the saturated and unsaturated fatty acids are $C_{16}$–$C_{18}$ with some shorter and longer chain length acids present. The resulting biologically active yellow-colored component(s) may be included in topical and systemic compositions for practicing the methods of this invention.

Compositions comprising emu oil, or a biologically active fraction thereof, and pharmaceutical preparations thereof, are intended for topical, oral or parenteral, e.g., subcutaneous injection, administration for prophylactic and/or therapeutic or cosmetic treatment. Preferably, the pharmaceutical compositions are administered topically, as an oil, paste, cream or salve.

For administration by parenteral injection the purified active fractions of emu oil may be used directly. Alternatively, the purified active fractions may be admixed with a neutral vehicle such as a vegetable oil, or acacia gum and injected as a dispersed suspension.

For oral administration, the emu oil, or a biologically active fraction thereof, can be employed in dosage forms such as gelatin capsules, liquid solutions, suspensions or elixirs.

Preferably, the compositions employed in each aspect of the present invention consist of 0.01–100% by weight of emu oil, or biologically active fraction thereof, by volume combined with 99.99–0% by weight of suitable diluents, carriers, excipients and other active agents. Repeated applications of the compositions to obtain the desired results are envisioned.

In accordance with the first aspect of the present invention, emu oil is employed in topical and parenteral formulations thereof and methods of using for the treatment of such skin conditions as dry skin (lack of dermal hydration), undue skin slackness (i.e., insufficient skin firmness) and insufficient sebum secretion. The methods and compositions are also effective in general preservating, conditioning, hydrating and protecting of skin, e.g., against wrinkles.

One or more additional substances which have therapeutic effects on the skin may also be incorporated in the compositions. Thus, in one embodiment of this invention the composition also contains one or more compounds capable of increasing cyclic-AMP levels in the skin. Suitable compounds include adenosine or a nucleic acid hydrolysate in an amount of about 0.1–1% and papaverine, in an amount of about 0.5–5%, both by weight based on the weight of the composition. Also suitable are β-adrenergic agonists such as isoproterenol, in an amount of about 0.1–2% or cyclic-AMP, in an amount of about 0.1–1%, again both by weight based on the weight of the composition. Other suitable types of additional active ingredients which may be incorporated in the compositions of this invention include any compounds known to have a beneficial effect on skin. Such compounds include retinoids such as Vitamin A, in an amount of about 0.003–0.3% by weight and chromanols such as Vitamin E or a derivative thereof in an amount of about 0.1–10% by weight, both based on the weight of the composition. Additionally, anti-inflammatory agents and keratoplastic agents may be incorporated in the cosmetic composition. A typical anti-inflammatory agent is a corticosteroid such as hydrocortisone or its acetate in an amount of about 0.25–5% by weight, or a corticosteroid such as dexamethasone in an amount of about 0.025–0.5% by weight, both based on the weight of the composition. A typical keratoplastic agent is coal tar in an amount of about 0.1–20% or anthralin in an amount of about 0.05–2% by weight, both based on the weight of the composition. Especially preferred additional components for purposes of the present invention are "active vitamin D compounds," parathyroid hormone (PTH) peptides or parathyroid hormone related peptides (PTHrP), each described in detail, below.

"Active vitamin D compounds" useful as additional substances in the cosmetic and dermatological compositions of the first and second aspects of the present invention are characterized structurally as side chain unsaturated and side chain saturated homologs of vitamin D, and preferably of 1,25-dihydroxyvitamin $D_3$, in which the side chain is elongated by insertion of one or more methylene units into the chain at the carbon 24 position. See U.S. Pat. No. 5,276,061, herein fully incorporated by reference. They may be represented, therefore, by the following general structure:

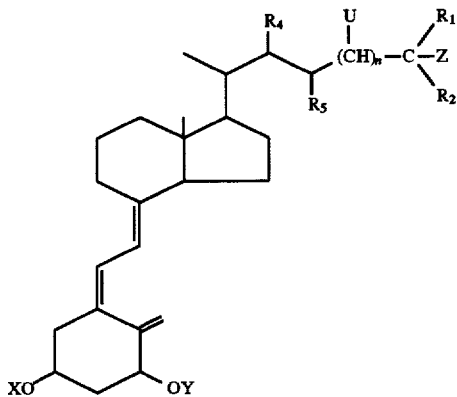

where $R_4$ and $R_5$ represent hydrogen or when taken together $R_4$ and $R_5$ represent a carbon-carbon double bond or a carbon-carbon triple bond, Z represents hydrogen, hydroxy or protected-hydroxy, U represents hydrogen, fluoro, hydroxy, protected-hydroxy or an alkyl group, X and Y which may be the same or different are hydrogen or a hydroxy-protective group, $R_1$ represents the group —(CH$_2$)$_q$—H or —CF$_3$ and $R_2$ represents the group —(CH$_2$)$_p$—H or —CF$_3$, and where n, q and p are integers having independently the values of 1 to 5, and $R_1$ and $R_2$ when taken together represent the group —(CH$_2$)$_m$— where m is an integer having the value of 2 to 5 (i.e., cycloalkyl).

The term "hydroxy-protective group" refers to any group commonly used for the protection of hydroxy functions during subsequent reactions, including, for example, acyl or alkylsilyl groups such as trimethylsilyl, triethylsilyl, t-butyldimethylsilyl and analogous alkylated silyl radicals, or alkoxyalkyl groups such as methoxymethyl, ethoxymethyl, methoxyethoxymethyl, tetrahydrofuranyl or tetrahydropyranyl. A "protected-hydroxy" is a hydroxy function derivatized by one of the above hydroxy-protecting groupings. "Alkyl" represents a straight-chain or branched hydrocarbon radical of 1 to 10 carbons in all its isomeric forms, such as methyl, ethyl, propyl, isopropyl, butyl, isobutyl, pentyl, etc., and the terms "hydroxyalkyl" and "fluoroalkyl" refer to such an alkyl radical substituted by one or more hydroxy or fluoro groups respectively. An acyl group is an alkanoyl group of 1 to 6 carbons in all its isomeric forms, or an aroyl group, such as benzoyl, or halo-, nitro- or alkyl- substituted benzoyl groups, or a dicarboxylic acyl group such as oxalyl, malonyl, succinoyl, glutaroyl, or adipoyl. The term "aryl" signifies a $C_6$ to $C_{14}$ aromatic group, e.g. a phenyl or naphthyl group.

It should be noted in this description that the term "24-dihomo" refers to the addition of two methylene groups at the carbon 24 position in the side chain. Likewise, the term "trihomo" refers to the addition of three methylene groups. Also, the term "26,27-dimethyl" refers to the addition of a methyl group at the carbon 26 and 27 positions so that for example $R_1$, and $R_2$ are ethyl groups. Likewise, the term "26,27-diethyl" refers to the addition of an ethyl group at the 26 and 27 positions so that $R_1$ and $R_2$ are propyl groups.

Specific and preferred examples of these compounds when the side chain is unsaturated (i.e., $R_4$ and $R_5$ represent a double bond) are: 24-dihomo-1,25-dihydroxy-22-dehydrovitamin $D_3$, i.e., the compound shown above, where X and Y are hydrogen, Z is hydroxy, n equals 3, and $R_1$ and $R_2$ are each a methyl group; 26,27-dimethyl-24-dihomo-1,25-dihydroxy-22-dehydrovitamin $D_3$, i.e., the compound shown above where X and Y are hydrogen, Z is hydroxy, n equals 3, and $R_1$ and $R_2$ are each an ethyl group; 24-trihomo-1,25-dihydroxy-22-dehydrovitamin $D_3$, i.e., the compound having the structure shown above, where X and Y are hydrogen, Z is hydroxy, n equals 4, and $R_1$ and $R_2$ are each a methyl group; 26,27-dimethyl-24-trihomo-1,25-dihydroxy-22-dehydrovitamin $D_3$, i.e., the compound shown above where X and Y are hydrogen, Z is hydroxy, n equals 4, and $R_1$ and $R_2$ are each an ethyl group; 26,27-diethyl-24-dihomo-1,25-dihydroxy-22-dehydrovitamin $D_3$, i.e., the compound shown above where X and Y are hydrogen, Z is hydroxy, n equals 3, and $R_1$ and $R_2$ are each a propyl group; 26,27-diethyl-24-trihomo-1,25-dihydroxy-22-dehydrovitamin $D_3$, i.e., the compound shown above where X and Y are hydrogen, Z is hydroxy, n equals 4, and $R_1$ and $R_2$ are each a propyl group; 26,27-dipropyl-24-dihomo-1,25-dihydroxy-22-dehydrovitamin $D_3$, i.e., the compound shown above where X and Y are hydrogen, Z is hydroxy, n equals 3, and $R_1$ and $R_2$ are each a butyl group; and 26,27-dipropyl-24-trihomo-1,25-dihydroxy-22-dehydrovitamin $D_3$, i.e., the compound shown above where X and Y are hydrogen, Z is hydroxy, n equals 4, and $R_1$ and $R_2$ are each a butyl group.

Specific and preferred examples of these compounds when the side chain is saturated (i.e., $R_4$ and $R_5$ each represent hydrogen) are: 1,25-dihydroxyvitamin $D_3$, 1,24-dihydroxyvitamin $D_3$, 24-dihomo-1,25-dihydroxyvitamin $D_3$, i.e., the compound shown above, where X and Y are hydrogen, Z is hydroxy, n equals 3, and $R_1$ and $R_2$ are each a methyl group; 26,27-dimethyl-24-dihomo-1,25-dihydroxy-vitamin $D_3$, i.e., the compound shown above where X and Y are hydrogen, Z is hydroxy, n equals 3, and $R_1$ and $R_2$ are each an ethyl group; 24-trihomo-1,25-dihydroxy-vitamin $D_3$, i.e., the compound having the structure shown above, where X and Y are hydrogen, Z is hydroxy, n equals 4, and $R_1$ and $R_2$ are each a methyl group; 26,27-dimethyl-24-trihomo-1,25-dihydroxy-vitamin $D_3$, i.e., the compound shown above where X and Y are hydrogen, Z is hydroxy, n equals 4, and $R_1$ and $R_2$ are each an ethyl group; 26,27-diethyl-24-dihomo-1,25-dihydroxy-vitamin $D_3$, i.e., the compound shown above where X and Y are hydrogen, Z is hydroxy, n equals 3, and $R_1$ and $R_2$ are each a propyl group; 26,27-diethyl-24-trihomo-1,25-dihydroxy-vitamin $D_3$, i.e., the compound shown above where X and Y are hydrogen, Z is hydroxy, n equals 4, and $R_1$ and $R_2$ are each a propyl group; 26,27-dipropyl-24-dihomo-1,25-dihydroxy-vitamin $D_3$, i.e., the compound shown above where X and Y are hydrogen, Z is hydroxy, n equals 3, and $R_1$ and $R_2$ are each a butyl group; and 26,27-dipropyl-24-trihomo-1,25-dihydroxy-vitamin $D_3$, i.e., the compound shown above where X and Y are hydrogen, Z is hydroxy, n equals 4, and $R_1$ and $R_2$ are each a butyl group.

Examples of the compounds of this invention wherein the side chain is saturated can be prepared according to the general process illustrated and described in U.S. Pat. No. 4,927,815 issued May 22, 1990, entitled "Compounds Effective in Inducing Cell Differentiation And Process For Preparing Same," the description of which is specifically incorporated herein by reference. Examples of the compounds of this invention wherein the side chain is unsaturated can be prepared according to the general process illustrated and described in U.S. Pat. No. 4,947,012 issued Jul. 11, 1989, entitled "Vitamin D Related Compounds And Process For Their Preparation," the description of which is specifically incorporated herein by reference. Examples of the compounds of this invention wherein $R_1$ and $R_2$ together represent a cyclopentano group can be prepared according to the general process illustrated and described in U.S. Pat. No. 4,851,401 issued Jul. 25, 1989, entitled "Novel Cyclopentano—Vitamin D Analogs," the description of which is specifically incorporated herein by reference.

Another synthetic strategy for the preparation of side-chain-modified analogues of 1α-dihydroxy-cholecalciferol and 1α,25-dihydroxyergocalciferol is disclosed in Kutner et al., *The Journal of Organic Chemistry* 53:3450–3457 (1988). In addition, the preparation of 24-homo and 26-homo vitamin D analogs is disclosed in U.S. Pat. No. 4,717,721 issued Jan. 5, 1988 entitled "Sidechain Homo-Vitamin D Compounds With Preferential Anti-Cancer Activity," the description of which is specifically incorporated herein by reference.

A class of peptides, termed PTH/PTHrP agonist and antagonist peptides, that have been shown to be capable of regulating cell proliferation and differentiation in mammals are useful as additional substances in the compositions and methods of the present invention. See PCT Published Application WO 92/04039, published Mar. 19, 1992. These peptides provide two important therapeutic properties, one involving inhibition of cell proliferation and enhancement of cell differentiation (the agonist activity), which is useful in the treatment of hyperproliferative disorders, such as psoriasis and cancer, and one involving enhancement of cell proliferation (the antagonist activity), which is useful for stimulating skin and hair growth, and in wound healing. In addition, some of the peptides possess the ability to enhance wound healing and stimulate hair growth based on in vivo wound healing activity or in vitro hair growth activity rather than strict agonist or antagonist activity in vitro. Thus, these peptides are useful as co-ingredients in the present invention, especially in the first, second, fifth, sixth and seventh embodiments of the invention.

Generally, peptides useful in the present invention include peptides that are at least 3, and more preferably at least 8, amino acids long, that have 10% or greater (more preferably, 50% or greater, and most preferably 75% or greater) homology with a region (preferably within the amino-terminal 34 amino acid region) of human parathyroid hormone or human parathyroid hormone related peptide (PTHrP). Examples of useful peptides include a 34-residue amino terminal fragment of human PTH (1–34) (herein, PTH (1–34)), synthetic fragment of PTHrP ([Tyr$^{34}$] PTHrP fragment (1–34) amide (herein, PTHrP (1–34)), [Nle$^8$, Nle$^{18}$, Tyr$^{34}$] bovine (3–34) PTH amide (herein, PTH (3–34)), [Tyr$^{34}$] bovine PTH (7–34) amide (herein, PTH (7–34)), human PTH (7–34), human, chicken, bovine, porcine or rat parathyroid hormone (herein, PTH (1–84) and human parathyroid-related protein (herein, hPTHrP (1–141)).

The peptides having agonist activity (PTH/PTHrP agonists) have particular application in the treatment of hyperproliferative skin disorders such as psoriasis and cancer. Agonist peptides are at least 3, and more preferably at least 8, amino acids long, have 10% or greater (more preferably, 50% or greater, and most preferably 75% or greater) homology with a region (preferably within the amino-terminal 34 amino acid region) of human parathyroid hormone or human PTHrP, and are capable of inhibiting proliferation or enhancing the differentiation in vitro of cultured human keratinocytes. These peptides may also be useful in the treatment of certain cancers, by the inhibition of cancer cell proliferation and by the induction of differentiation. Preferred agonist peptides include PTH (1–34), PTH (3–34) or PTHrP (1–34) and their amide derivatives.

The peptides having antagonist activity (PTH/PTHrP antagonists) are generally useful for enhancing proliferation of mammalian cells. Antagonist peptides are at least 3, and more preferably at least 8, amino acids long, have 10% or greater (more preferably, 50% or greater, and most preferably 75% or greater) homology with a region (preferably within the amino-terminal 34 amino acid region) of human parathyroid hormone or human parathyroid hormone related peptide, and are capable of blocking the differentiation or the inhibition of proliferation in vitro of cultured human keratinocytes by PTH (1–34) or 1,25(OH)$_2$D$_3$ or PTHrP (1–34). A preferred PTH/PTHrP antagonist peptide is PTH (7–34) and its amide derivative.

Other PTH/PTHrP peptides are useful for enhancing proliferation of a mammalian cell. These peptides are at least 3, and more preferably at least 8, amino acids long, have 10% or greater (more preferably, 50% or greater, and most preferably 75% or greater) homology with a region (preferably within the amino-terminal 34 amino acid region) of human parathyroid hormone or human parathyroid hormone related peptide, and are capable of enhancing wound healing in an in vivo skin punch assay. Preferred peptides for this aspect of the invention include PTH (1–34), PTH (7–34), PTH (1–84), hPTHrP (1–141), PTHrP (1–34), or PTHrP (7–34). These peptides have particular application as co-ingredients in the methods and compositions for enhancing wound healing and may also have applications in promoting skin growth in patients with burns or skin ulcerations as well as stimulating epidermal regrowth in people who have decreased epidermal cell proliferation due to aging.

Hair growth is stimulated in mammals by PTH/PTHrP peptides that are at least 3, and more preferably at least 8, amino acids long, have 10% or greater (more preferably, 50% or greater, and most preferably 75% or greater) homology with a region (preferably within the amino-terminal 34 amino acid region) of human parathyroid hormone or human parathyroid hormone related peptide, and are capable of stimulating hair growth in vitro. A preferred peptide in this aspect of the invention is PTH (7–34). These peptides have application as a co-ingredient in the methods of promoting new hair growth or stimulating the rate of hair growth, and can be applied in an amount of about 0.01 μg to about 100 μg per gm of composition.

When selecting a candidate PTH/PTHrP agonist or antagonist peptide for the present invention, a preferred first step is to choose a peptide which includes a fragment which has at least 10%, and more preferably 50% or greater, homology with an 8 or greater amino acid long fragment within the amino terminal 34 amino acid region of human PTH or PTHrP. By "homology" is meant amino acid sequence identity. Because of the high degree of homology among human PTH and PTH of other species, non-human as well as human fragments or analogs can be used. For purposes of the present invention, percent homology is determined by lining up a sequence of interest (SOI) with a selected region (REGION) of human parathyroid hormone (hPTH) or parathyroid hormone related peptide (PTHrP) directly comparing amino acids of the two sequences beginning at the amino terminus of each sequence; and calculating the ratio of:

$$\frac{\text{Number of amino acids in the } SOI \text{ that are identical to the REGION}}{\text{Number of amino acids in the REGION}}$$

Homologous peptides must also be at least 3, and more preferably at least 8, amino acids long. Further, the fragment can be modified in any of a variety of standard chemical ways, e.g., the carboxy-terminal amino acid residue can be made into a terminal amide group; the amino-terminal residue can be modified with groups to, e.g., enhance lipophilicity; the peptide can be chemically glycosylated to increase solubility or in vivo half-life; and D-amino acids can be substituted for L-isomers in the peptide.

Candidate peptides are tested for suitability as inhibitors of cell proliferation and enhancers of differentiation using cultured human keratinocytes, as described in U.S. Pat. No. 5,037,816. Those peptides which inhibit proliferation and induce differentiation in cultured keratinocytes are those potentially useful as therapeutic agents in treating disorders, e.g., psoriasis, precancer, such as actinic keratoses, and cancer, where suppression of cell proliferation is desired.

Candidate peptides may be tested for suitability as enhancers of cell proliferation using cultured human keratinocytes. Those peptides which block the effect of agonist peptides or 1,25(OH)$_2$D$_3$ on cultured keratinocyte proliferation are those potentially useful as therapeutic agents in treating disorders, e.g., wounds, burns, or skin ulcerations, where maintenance or stimulation of cell proliferation is desired.

Candidate peptides may be tested for their ability to enhance wound healing by carrying out a skin punch biopsy test, described in PCT Published Application WO92/04039, published Mar. 19, 1992.

Candidate peptides may be tested for suitability as stimulators of hair growth using an in vitro hair growth assay, such as is described in PCT Published Application WO92/04039. Those peptides which stimulate hair growth in vitro are those potentially useful for co-administering with emu oil for stimulating hair growth in vivo.

Compositions for use in the treatment of such skin conditions as dry skin (lack of dermal hydration), undue skin slackness (i.e., insufficient skin firmness) and insufficient sebum secretion, as well as compositions effective in general preservating, conditioning, hydrating and protecting of skin, e.g., against wrinkles treatment of skin, preferably comprise emu oil, or a biologically active fraction thereof, and optionally one or more side chain unsaturated or active vitamin D compounds, and/or one or more PTH/PTHrP antagonists, and a suitable carrier. A preferred amount of emu oil is about 0.01 to 99.99% by weight. Lesser amounts of the biologically active fractions can be used. A cosmetically effective amount of active vitamin D compounds for use in accordance with this invention is from about 0.01 μg to about 100 μg per gm of composition. A concentration of about 10 μg active vitamin D compound per gm of the composition is preferred. A cosmetically or dermatologically effective amount of a PTH/PTHrP agonist or PTH/PTHrP antagonist peptide for use in accordance with this invention is about 0.01 μg to about 100 μg per gm of composition. A concentration of about 10 μg PTH/PTHrP agonist or antagonist peptide per gm of composition is preferred.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired.

Creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight.

Lotions may be conveniently prepared by dissolving the active ingredient, in a suitable high molecular weight alcohol such as propylene glycol or polyethylene glycol.

The tissue healing compositions comprise emu oil or a biologically active fraction thereof in admixture with an active vitamin D compound or a PTH/PTHrP antagonist peptide, and may include a conventional pharmaceutical carrier or excipient. In addition, these compositions may include other medicinal agents, growth factors, wound sealants, carriers, etc., that are known or apparent to those skilled in the art. The tissue healing compositions of the invention are administered to a warm-blooded animal, such as human, already suffering from a wound, oxidative skin damage, skin lesions or burns, in an amount sufficient to allow the healing process to proceed more quickly than if the host were not treated. Amounts effective for this use will depend on the severity of the wound, sore or burn, and the general state of health of the patient being treated. Maintenance dosages over a prolonged period of time may be adjusted as necessary. For veterinary uses, higher levels may be administered as necessary.

In the case of an animal suffering from decreased hair growth, the compositions of the invention are administered in an amount sufficient to increase the rate of hair growth. Amounts effective for this use will depend on the extent of decreased hair growth, and the general state of health of the patient being treated. Maintenance dosages over a prolonged period of time may be adjusted as necessary. For veterinary uses, higher levels may be administered as necessary.

In the case of an animal suffering from hypopigmentation disorder(s), the compositions of the invention are administered in an amount sufficient to increase the pigmentation of affected skin tissue. Amounts effective for this use will depend on the extent of hypopigmentation, and the general state of health of the patient being treated. Maintenance dosages over a prolonged period of time may be adjusted as necessary.

For application as skin tanning enhancers, the compositions of the invention are administered in an amount sufficient to enhance the tanning of a subject's skin. The compositions can be applied in conjunction with exposure to the sun, or artificial ultraviolet radiation such as a suntanning bed, or the compositions can be applied without subsequent exposure to the sun or tanning lights. In either instance, the benefit of an enhanced skin tan will be achieved.

Animals which may be treated according to the present invention include all animals which may benefit therefrom. Such animals include, but are not limited to, mammals such as humans.

The efficacy of emu oil in accordance with this invention was determined by the following procedure. The following example is illustrative, but not limiting, of the method and compositions of the present invention. Other suitable modifications and adaptations of the variety of conditions and parameters normally encountered in clinical therapy and obvious to those skilled in the art are in the spirit and scope of the invention.

EXAMPLE

Adolescent C57 BL/6 mice that were six to eight weeks old with all of their hair follicles arrested in telogen for several weeks were selected. The hair from the back skin was removed by a wax/rosin mixture as previously described by R. Paus et al., *J. Invest. Dermatol.* 103:143–147 (1994). After depilation, three mice receive on the nape of the neck topically, 0.1 ml of emu oil and 2 mice received topically 0.1 ml of corn oil in a double-blinded fashion. For the next 19 days, the animals received a single topical application of either emu oil or corn oil. On day 18, the animals received $^3$-Thymidine intraperitoneally as previously described by M. F. Holick et al., *Proc. Natl. Acad. Sci. USA* 91:8014–8016 (1994). Twenty-four hours later the animals backs were photographed and the animals were then sacrificed and the skin removed for analysis.

Figure 2:
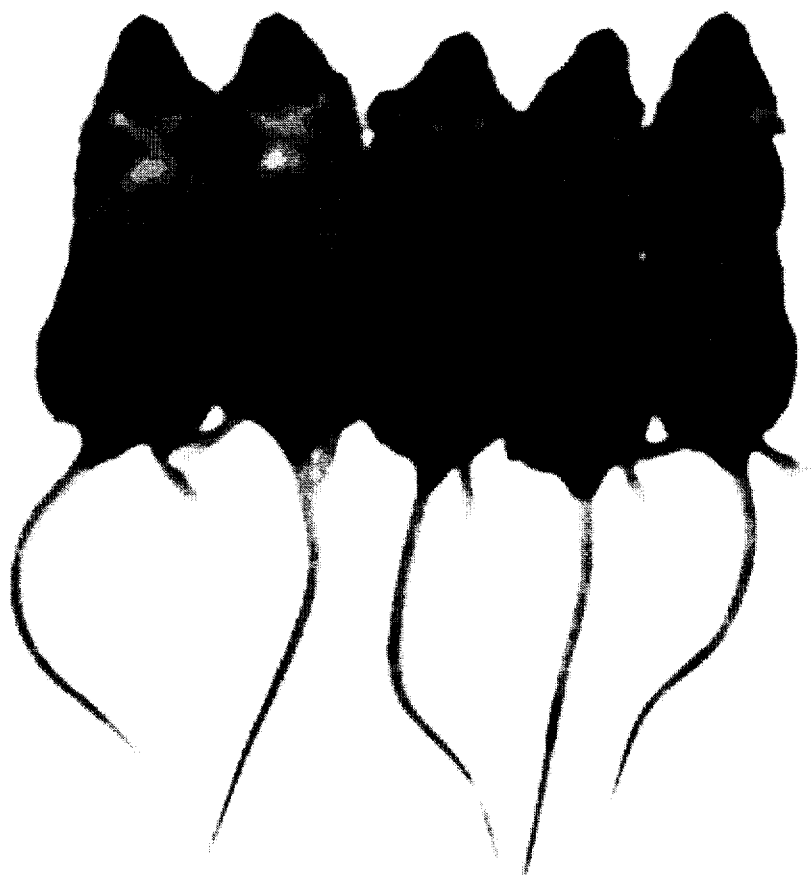
FIG. 2 is a photograph of C57 BL/6 mice after 19 days of topical application of 0.1 ml of either corn oil (two mice on left side of picture) or emu oil (three mice on right side of picture) on the nape of the neck daily.

An evaluation of the incorporation of $^3$H-thymidine in the epidermis revealed that the animals that were treated with emu oil had a significant 29% increase in $^3$H-thymidine incorporation when compared to the control animals that received a topical application of corn oil (FIG. 1). The photograph of the animals just before sacrifice demonstrated increased pigmentation and hair over the upper back region of the three mice that received emu oil compared to the two mice that received corn oil (FIG. 2). A histologic evaluation confirmed the visual observation. There was a more marked increase in the size and length of the hair follicles and thickness of the skin in the mouse skin that was treated with emu oil when compared to mouse skin treated with corn oil.

It can be concluded from these studies that the topical application of emu oil increased the synthesis of DNA in the epidermis which is a measure of increase in the proliferative activity of the epidermis. The increase in pigmentation and hair in the photograph of animals receiving emu oil demonstrates that the topical application of emu oil can stimulate melanogenesis and hair follicle development and growth. The histological analysis demonstrating an increase in the thickness of the epidermis and size and length of the hair follicle provides strong evidence that the topical application of emu oil stimulates skin growth, hair growth and induces the proliferation of the cells around the hair follicle.

Having now fully described this invention it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed Is:

1. A method of inducing proliferation of mammalian skin cells, comprising contacting said cells by topically applying emu oil or a biologically active fraction thereof to the skin of a mammal in an amount effective to induce proliferation of said skin cells.

2. The method of claim 1, wherein said skin cell is an epidermal cell.

3. The method of claim 2, wherein said epidermal cell is an epidermal cell selected from the group consisting of:

i) keratinocytes ii) melanocytes and iii) hair follicles.

4. The method of claim 1, wherein said skin cell is a dermal cell.

5. The method of claim 4, wherein said dermal cell is a dermal fibroblast.

6. The method of claim 1, wherein said proliferation of said mammalian cell is induced in vivo.

7. The method of claim 1, wherein said proliferation of said mammalian cell is induced in vitro.

8. The method of claim 1, wherein said emu oil or biologically active fraction thereof are topically administered in the form of an oil, paste, cream or salve.

9. The method of claim 1, wherein said biologically active fraction is prepared by:

fractionating emu oil diluted with hexane using a florisil column;

eluting said column successively with hexane, dichloromethane and 10% methanol in dichloromethane; and separating a biologically active component from the 10% methanol in dichloromethane fraction.

10. A method of inducing proliferation of mammalian skin cells, comprising topically applying emu oil to mammalian skin cells in an amount effective to induce proliferation of said skin cells.

* * * * *